US005290697A

United States Patent [19]
Shabtai et al.

[11] Patent Number: 5,290,697
[45] Date of Patent: Mar. 1, 1994

[54] SPECIES OF A MICROORGANISM OF THE GENUS RHODOCOCCUS

[75] Inventors: Joseph Shabtai, Ramat Hasharon; Gideon Fleminger, Rehovot; Joseph Fleming, Nes Ziona, all of Israel

[73] Assignee: The Israel Electric Corporation Ltd., Haifa, Israel

[21] Appl. No.: 876,063

[22] Filed: Apr. 29, 1992

Related U.S. Application Data

[62] Division of Ser. No. 790,582, Nov. 8, 1991, Pat. No. 5,231,018.

[30] Foreign Application Priority Data

Oct. 12, 1990 [IL] Israel ........................................ 96611

[51] Int. Cl.$^5$ ............................. C12N 1/20; C12R 1/01
[52] U.S. Cl. ................................. 435/252.1; 435/822
[58] Field of Search ............................. 435/252.1, 822

[56] References Cited

U.S. PATENT DOCUMENTS 5,132,219  7/1992  Kilbane, II ........................ 435/252.1
5,179,014  1/1993  Watanabe ............................ 435/170

OTHER PUBLICATIONS

"ATCC Catalogue Bacteria & Bacteriophages" 17th Ed 1989 pp. 183–188.

Primary Examiner—Herbert J. Lilling
Attorney, Agent, or Firm—Helfgott & Karas

[57] ABSTRACT

A novel species of microorganism of the Genus Rhodoccocus filed as strain GIN-1 and deposited under No. 40340 at the National Collections of Industrial and Marine Bacteria, Ltd. (NCIMB) at Aberdeen. Scotland.

1 Claim, 15 Drawing Sheets

FIG. 3A
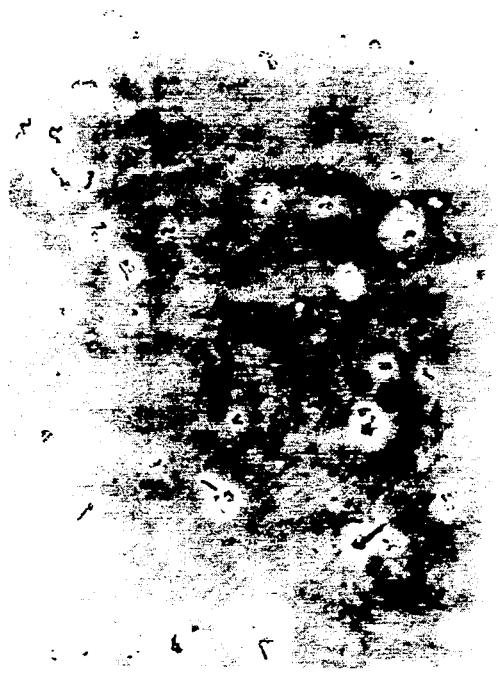
FIG. 3B
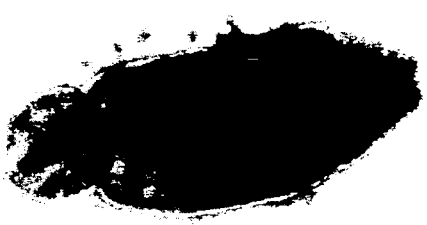
FIG. 3C
FIG. 3D

FIG. 9A
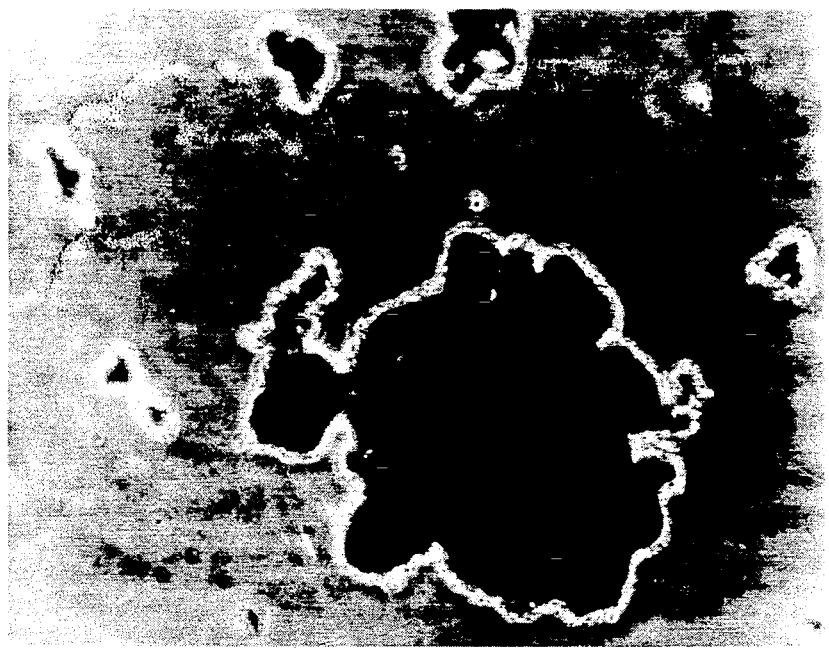
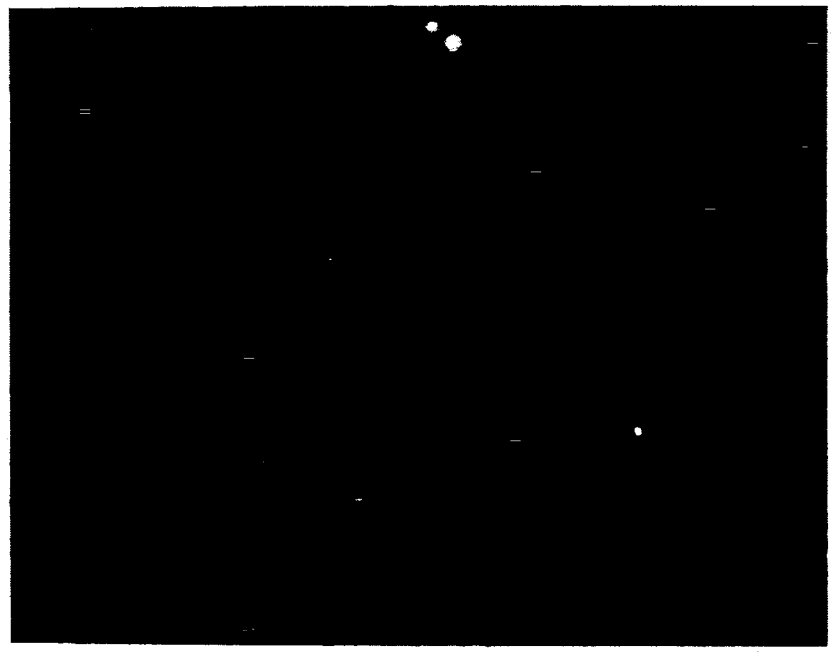
FIG. 9B

FIG. 9C
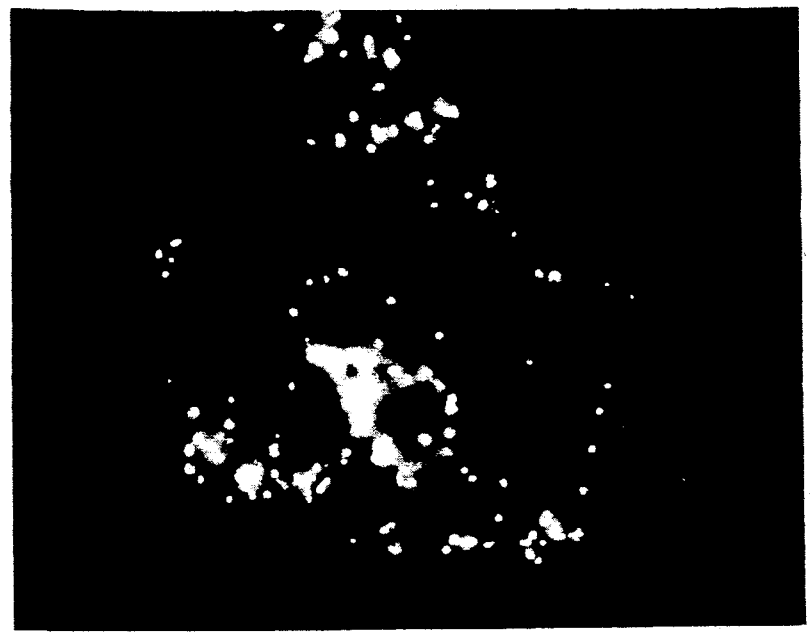
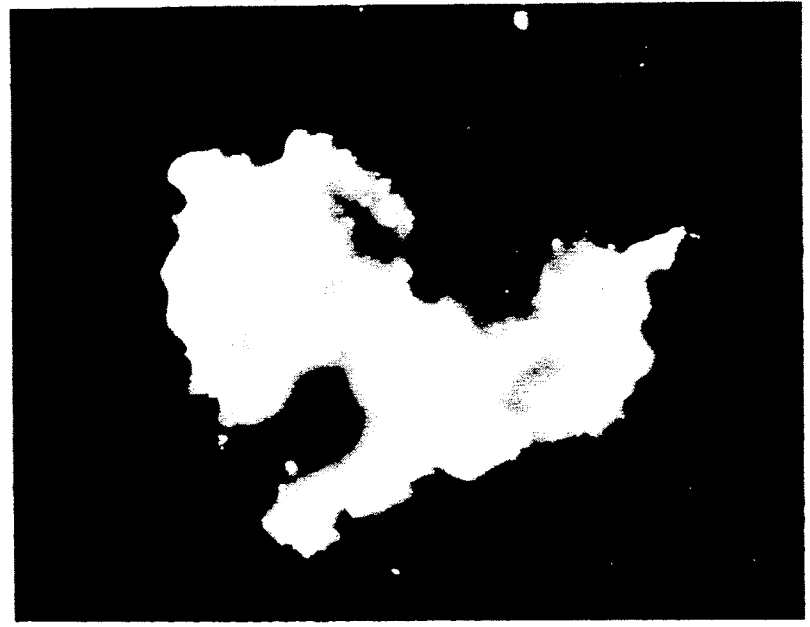
FIG. 9D

FIG. IOA
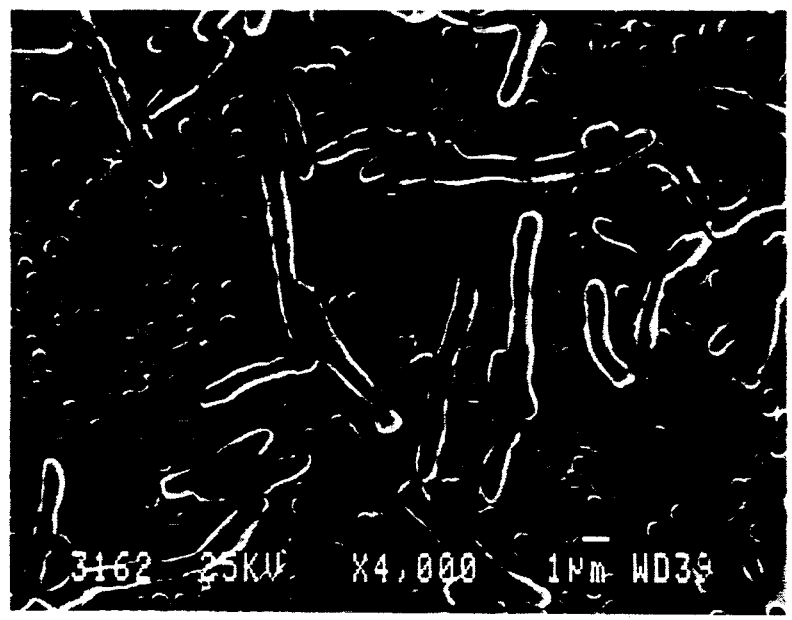
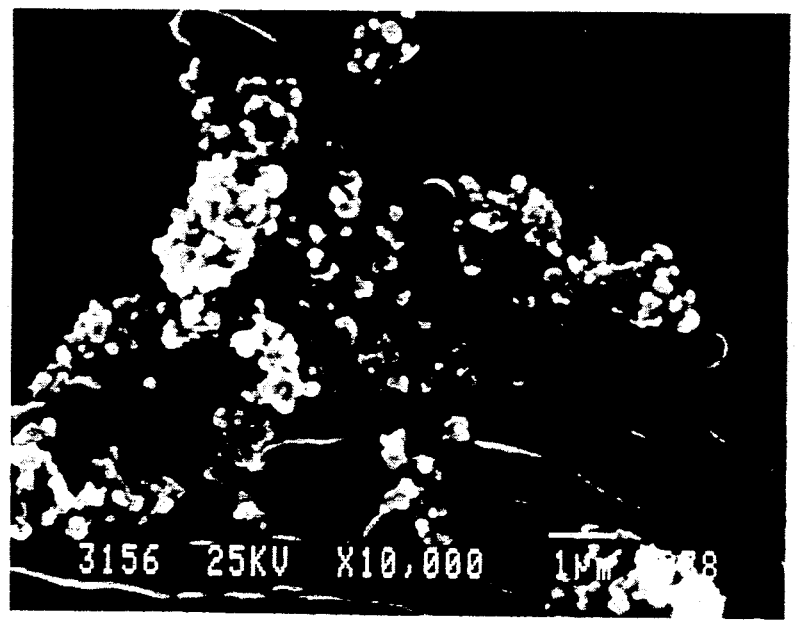
FIG. IOB

FIG. 12A
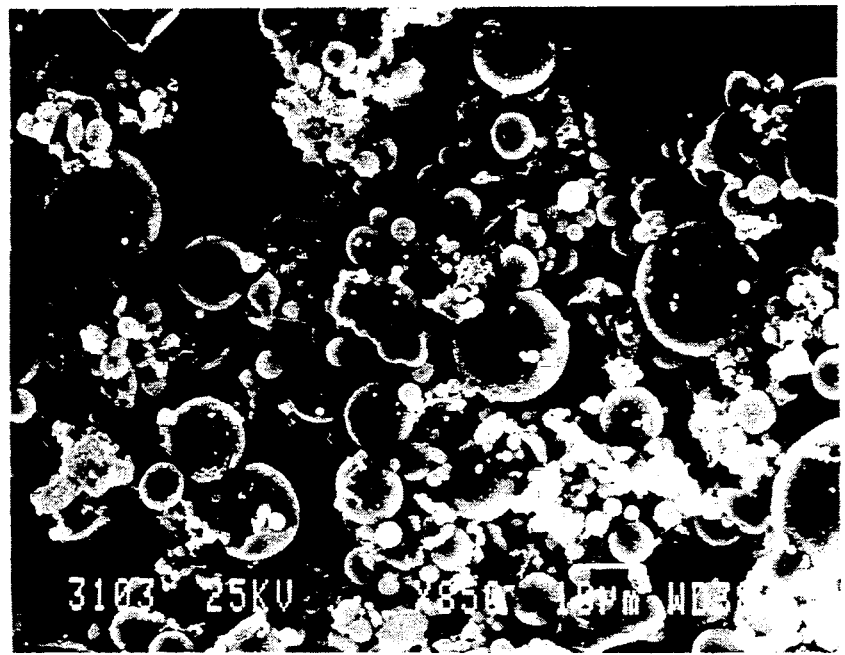
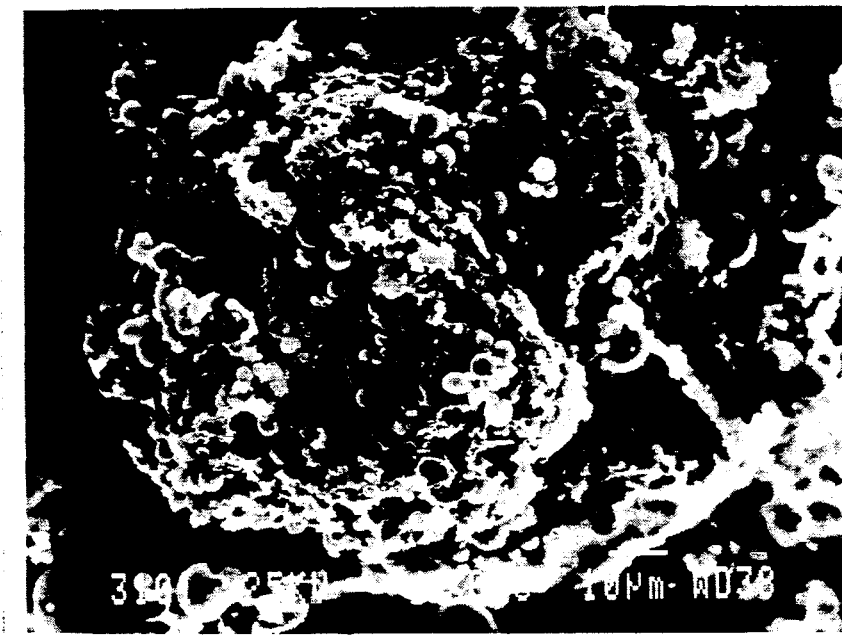
FIG. 12B

FIG. 13A
FIG. 13B

SPECIES OF A MICROORGANISM OF THE GENUS RHODOCOCCUS

This is a division of application Ser. No. 790,582, filed Nov. 8, 1991 now U.S. Pat. No. 5,231,018.

FIELD OF THE INVENTION

The present invention is generally in the field of treatment of coal fly ash, for the removal therefrom of metal oxides. The removed metal oxides may, if desired, be separated from each other and purified to provide commercially valuable amounts of elementary metals or metal compounds and the decontaminated coal fly ash may be recycled for repeated use or else be disposed in landfills. The removed metal oxides may be separated from each other and purified to provide commercially valuable amounts of metals or metal compounds.

The invention also concerns a new bacterial strain, its isolation from a man-made environment and its use for the removal of metal oxides from coal fly ash.

BACKGROUND OF THE INVENTION

Coal fly ash is known to contain a variety of metals such as aluminium, titanium, zinc, copper, cobalt and others, usually in the form of insoluble metal oxides. Many of these metals and their oxides are environmentally hazardous, in that when the coal fly ash is disposed in land fills, in the sea or in other waterways metal oxides are leached out and find their way into potable water and into animal and vegetable food for human consumption. For example, it has been reported that food sources contaminated with aluminium may affect the brain and trigger off Alzheimer disease.

It is thus evident that the disposal of coal fly ash which in many industrialized nations amount to millions of tons yearly, poses a serious environmental problem.

Depending on their nature and concentration, the metals present in coal fly ash as oxides may in themselves be of industrial value. Accordingly, the gravity of the environmental problem arising in connection with the disposal of coal fly ash on the one hand, and the fact on the other hand that the recovery of metals from such waste products may in itself be of economic value, both of which have long been released, have for a long time prompted investigators in the field to look for processes for the removal of metal oxides from coal fly ash.

By some proposals, metals are extracted from coal fly ash by conventional chemical leaching processes which, however, are not economically attractive as they require the use of strong acids and other chemicals and expensive acid-proof equipment. It has further been proposed in relation to coal fly ash to employ bioleaching methods, but the known microorganisms utilized for this purpose require extremely acidic conditions for growing and, moreover, also produce acids themselves so that here again similar processing problems arise. Moreover, in addition to being technologically onerous, these known chemical and biotechnological, acid-consuming processes are in themselves ecologically hazardous due to the need of handling and disposing large amounts of acids.

In principle, biotechnological leaching could provide a satisfactory and environment friendly solution to the problem of removing metal oxides from coal fly ash, provided it is operated under mild conditions. However, hitherto no suitable microorganism was found that would combine efficient extraction of metal oxides with environment friendly operating conditions.

It is the object of the present invention to provide an ecologically and economically viable process for the bioextraction of metal oxides from coal fly ash.

It is a further object of the present invention to provide microorganisms that can be used for that purpose.

SUMMARY OF THE INVENTION

The present invention is based on the finding that certain microorganisms capable of growing in aqueous saline solutions at a pH within the range of from 5 to 8 are capable of adsorbing to metal oxides in an aqueous environment.

Accordingly, the present invention provides a process for the extraction of metal oxides from coal fly ash, comprising forming a suspension of the coal fly ash in an aqueous saline solution having a pH within the range of from 5 to 8 , forming a reaction mixture by adding to such suspension pure culture cells of a microorganism strain capable of growing in aqueous saline solution and of binding to metal oxide, incubating the said reaction mixture for a period of time sufficient for the formation of microorganism cells/metal oxide adsorbate agglomerates and separating such agglomerates from the reaction mixture.

If desired, the separated microorganism cell/metal oxide adsorbate agglomerates may be processed for the recovery of metal oxide therefrom, e.g. by heating the separated agglomerates to a temperature at which the microorganism is burnt off.

In accordance with one embodiment of the invention the said suspension of the coal fly ash is inoculated with a small amount of microorganism cells and the microorganism is grown therein whereby the said reaction mixture is formed.

In accordance with another embodiment of the invention, a desired quantity of the microorganism cells is first grown in aqueous saline solution and is then added to the said suspension of coal fly ash to form the said reaction mixture.

The aqueous saline solution required for practising the invention may be sea water or else be constituted from fresh water supplied by a standard water supply, or even from distilled water, in which a desired amount of a salt mixture of suitable composition is dissolved.

The incubation temperature is preferably within the range of from about 25° to about 32° C., and depending on the circumstances the incubation period may be very short, e.g. 30 seconds, or relatively long, e.g. 1 hour. Preferably the reaction mixture is agitated during incubation.

At the end of the incubation the microorganism cell/metal oxide adsorbate agglomerates are separated from the reaction mixture. For example, sink-float classification methods may be employed such as slow centrifugation in the range of about 200 rpm, spontaneous flotation or induced flotation. In any of these sink-float classification methods the microorganism cell/metal oxide adsorbate agglomerates will form the sink fraction while the bulk of the remaining solids suspended in the reaction mixture will float.

Instead of using sink-float classification, magnetic separation may be used for the removal of the microorganism cell/metal oxide adsorbate agglomerates from the reaction mixture. To this end the microorganism cells must be associated with a paramagnetic compound such as magnetite.

Thus, by a modification of the above defined process, the invention provides a process for the extraction of metal oxide from a coal fly ash comprising forming a first suspension of coal fly ash in an aqueous saline solution, separately growing a pure culture of a microorganism of the kind specified in an saline solution having a pH of 5 to 8, admixing with the pure culture a paramagnetic compound capable to associate with cells of the microorganism to obtain a second aqueous suspension holding microorganism cell/paramagnetic compound complex particles, admixing the first and second suspensions to produce an aqueous reaction mixture, incubating the aqueous reaction mixture at a temperature of from 25°–32° C. to produce a third suspension containing microorganism cell/paramagnetic compound metal oxide complex adsorbate agglomerate, subjecting the third suspension to magnetic separation whereby the complex adsorbate is separated from the third suspension, and dissociating and separating the paramagnetic compound from the complex adsorbate whereby a microorganism cell/metal oxide adsorbate is obtained.

If desired, the microorganism cell/metal oxide adsorbate so obtained may be processed for the recovery of metal oxide therefrom., e.g. by heating to a temperature at which the microorganism is burnt off.

Preferably, the paramagnetic compound capable of associating with the microorganism cells of the kind specified is magnetite.

The aqueous saline solution used both for growing the pure microorganism dell culture and for forming the first suspension nay be sea water or else be constituted from fresh water supplied by a standard water supply, or even from distilled water, to which a desired amount of a salt mixture of suitable composition is added.

Magnetic separation is a known technique which need not be described in detail. In practising the above modification of the process according to the invention, a magnetic field may be applied across the vessel holding the reaction mixture whereby upon withdrawal of the third aqueous suspension the complex adsorbate is retained on a wall of the vessel. The retained adsorbate substance is then flushed out and the resulting aqueous suspension of complex adsorbate may be processed for the recovery of the latter which may then be resuspended and subjected to treatment by which the paramagnetic compound is dissociated from the complex. Alternatively, the above aqueous suspension resulting from flushing out the complex adsorbate substance may be subjected directly to such treatment.

The dissociation treatment is essentially mechanical. For example, dissociation of the paramagnetic compound from the complex adsorbate may be achieved by intensively stirring the complex adsorbate in aqueous suspension, e.g. by means of a magnetic stirrer, by which the paramagnetic compound is dissociated from the complex adsorbate leaving behind a floating microorganism cell/metal oxide adsorbate while the paramagnetic compound collects as sediment.

It has been found in accordance with the present invention that different metal oxides differ from each other by the kinetics of adsorption of microorganism cells of the kind specified. It is accordingly possible in accordance with the present invention to selectively remove a particular oxide or mixture of oxides from a coal fly ash, in that the incubation time of the reaction mixture is so adjusted that selective adsorption occurs. For example, titanium oxide ($TiO_2$) can be removed preferentially from coal fly ash with a microorganism strain of the kind specified by limiting the incubation time to say between about 30 seconds and about 5 minutes. After removal of the $TiO_2$, incubation may be repeated for the removal of another oxide, say $Al_2O_3$, and this procedure may be repeated several times.

Alternatively, it is possible in accordance with the invention to apply a relatively long incubation time, say 1 hour, sufficient for the microorganism cells to adsorb to practically all metal oxides present in the coal fly ash, whereby a mixture of metal oxides is obtained which may then be subjected to separation operations by methods known per se.

The raffinate remaining after the removal of metal oxides from a coal fly ash in accordance with the invention, consists essentially of unburned carbon, silicium oxide and possibly some silicates. If desired this raffinate may be recycled as fuel or else be safely disposed in landfills.

The microorganisms utilized for carrying out the processes according to the present invention are preferably selected from the group Gram-positive marine bacterial strains.

In accordance with the present invention a particularly useful strain of such microorganism has been isolated from a man-made environment and identified. Thus, by another aspect the present invention provides a pure culture of a Gram-positive bacterial strain designated herein as AGIN-1, being a member of the genus Rhodococcus. A sample of the GIN-1 strain was deposited under No. 40340 at the National Collections of Industrial and Marine Bacterial Ltd. (NCIMB) at Aberdeen, Scotland.

BRIEF DESCRIPTION OF THE DRAWINGS

In the following the invention will be described with reference to the annexed drawings in which:

FIGS. 3A, 3B, 3C and 3D are phase, fluorescent and two electron micrographs of the GIN-1 strain of the present invention, obtained as described in Example 5;

FIGS. 9A and 9D are regular phase and background fluorescence micrographs of $TiO_2$ particles suspended in sea water in the absence of GIN-1 cells, as described in Example 10;

FIGS. 9C and 9D are regular phase and background fluorescence micrographs of GIN-1 cells adsorbed to $TiO_2$ particles as described in Example 10;

FIGS. 10A and 10B show respectively GIN-1 cells in culture and GIN-1 cells adsorbed to $TiO_2$ particles in culture, as described in Example 10;

FIGS. 12A and 12B show two electron micrographs of coal ash material without bacterial cells as described in Example 13;

FIGS. 13A and 13B show two electron micrographs of coal ash adsorbed to GIN-1 cells as described in Example 13;

SPECIFIC DESCRIPTION OF THE INVENTION

The present invention will now be described in more detail in the following non-limiting Examples and their accompanying Tables and Figures.

EXAMPLE 1: Isolation of microorganisms capable of adhering to coal ash components a. Sources of microorganisms About 20 samples of water effluents, reservoirs and soil were collected at or nearby the site of the coal-fired Hadera power station in liadera, Israel. Each of the samples was subjected to a preliminary microscopic examination. Additional characterization of the effluent water samples was carried out by measuring the pH and conductivity in these samples using standard methods and apparatus therefor.

b. Coal Ash samples

A 15 kg sample of coal ash mixture was obtained from the aforesaid Hadera power station and stored at room temperature at the Department of Biotechnology, Tel-Aviv University, Tel-Aviv, Israel.

c. Enrichment cultures of the isolated microorganism strains

One of the above-noted effluent water samples originating from a precipitation pool, was inoculated into a complex enrichment medium containing 25% (w/v) of the above-noted coal ash mixture. The complex enrichment medium was based on sea water and was formulated as follows:

1 liter sea water sterilized by filtration with a 0.22 micron filter
20 ml of 25% (w/v) sterile solution of nutrient broth
10 ml of 10% (w/v) sterile $NH_4Cl$ solution
10 ml of 0.5 M sterile potassium phosphate buffer solution pH=6.5
250 gr coal ash.

The inoculated enrichment medium was subdivided into separate test cultures, and the enrichment procedure leading to the isolation of the microorganism strains was carried out as follows:

i) First stage enrichment

Figure 1:
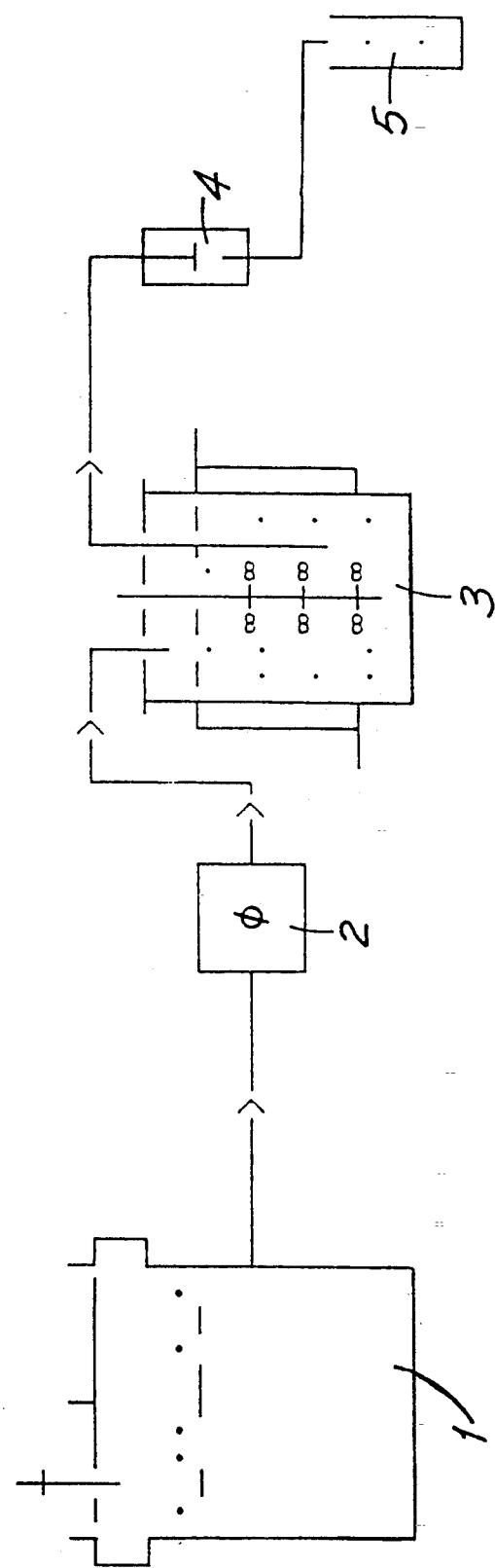
FIG. 1 is a schematic layout of a continuous microorganism enrichment and bioadsorption system according to the invention as described in Example 1.

A continuous enrichment system was used which is schematically illustrated in FIG. 1. As shown the system comprises a reservoir 1 holding the above complex enrichment medium, a peristaltic pump 2, an adsorption reactor 3, a reactor outlet level regulator 4 and a plurality of sampling beakers 5 for analyzing liquid.

The cultures were initially incubated at different temperatures: 25° C., 30° C., 32° C., 35° C. and 40° C. under gyrotory agitation (200 rpm). Growth of the microorganisms was observed microscopically and by viable plating.

A 10 ml sample of each of these cultures was inoculated into the above continuous enrichment system. Reaction 3 in the system is based on a continuous stirred thermoregulated (32° C.) glass vessel (500 ml) in which a sample of the adsorbing material is suspended in the complex sea water medium. The sample containing the candidate cells to be adsorbed were injected into the vessel and allowed to interact with the solid particles for 15 minutes. Following this adsorption stage, filtered complex sea water medium was fed continuously ($D=0.5$ $h^{-1}$) into the adsorption reactor to flush and wash out non-adsorbed cells with about 10 volumes of medium per reactor liquid volume. Final flushing was carried out with filtered sea water only. Samples of the retained particulate coal ash matter were withdrawn and spread on nutrient agar plates for the isolation of the coal ash adherent strains.

ii) Second stage enrichment

Seven pure cultures were grown and subsequently reinjected into the continuous adsorption reactor, in which pure titanium dioxide replaced the coal ash. After adsorption stage, the reactor was flushed with complex medium followed by washing with filtered sea water for removal of non-adsorbed cells. Samples of the retained $TiO_2$ particles were spread on nutrient agar plates for final isolation of adherent microorganisms.

iii) Pure cultures

Pure cultures of the $TiO_2$ adherent microorganisms selected following the above second stage enrichment procedure, were obtained as follows: Samples from the selected cultures were taken and inoculated into $TiO_2$-containing fresh cultures to verify their adsorption characteristics to coal ash and $TiO_2$. The same above-noted complex medium was used. Coal ash was added to a final concentration of 25% (w/v), and $TiO_2$ to 10% (w/v). These cultures were incubated at different temperatures under gyrotory shaking. The temperature range of 28°-32° C. was found to support the best growth of most of the isolates.

iv) Results of isolation procedure

Seven microbial strains with the selected coal ash and $TiO_2$ adsorption capability were isolated, pure cultures were prepared and stocks were made for future examinations.

All seven isolates obtained under the above procedure were found to be Gram positive bacteria, indicating possible adaptability of this group of bacteria to the selective pressure in the enrichment cultures which pressure is represented by the metal oxides, in general, which are present in the coal ash and the $TiO_2$, in particular. This adaptability is considered to be related to the polysaccharide envelope on the outer surface of these bacteria which provides the bacterial cells with a capability for binding the metal oxides, i.e. adherence, but prevents these oxides from adversely affecting the cells.

Two of the isolated bacteria, which had been previously found to adhere to coal ash components, in particular to $TiO_2$, were characterized microscopically with respect to their cellular and colonial morphology, and some basic aspects of their physiology and preliminary preservation conditions. Both bacteria produce pigments and can be easily distinguished from other strains or contaminants.

Figure 2:
FIG. 2 is a photograph of pure culture colonies of the GIN-1 strain according to the present invention obtained as described in Example 1.

One of the isolated bacteria was selected for the purposes of carrying out the hereinafter described methods of metal oxide extraction from coal ash of the present invention. This selection was made on the basis of observations with respect to its characteristics of particularly good growth, survival and adherence to $TiO_2$. This strain produces a salmon-pink colored pigment and was given the name GIN-1. Pure cultures of the GIN-1 strain as grown on semi-solid nutrient agar culture medium containing petri plates are represented in FIG. 2. It should be noted that the typical salmon-pink colored pigment also appeared in liquid cultures of the GIN-1 strain.

EXAMPLE 2: Microbiological characterization of GIN-1

The GIN-1 strain as purified according to Example 1 was further characterized as follows:

i) Nutrient requirements and establishment of Growth medium

The first essential step in the characterization of the bacterium was to establish an optimal growth medium in which its adherence capability to the selected oxides is fully expressed. This medium will serve routine cultivation of the bacterium.

Cultivation of GIN-1 on different liquid or semisolid media was carried out in order to examine which carbon sources are utilized by the bacterium. In this respect, sugars, alcohols, organic acids, triglycerides, hydrocarbons and some other complex available mixtures (all of scientific grade purity) such as protein hydrolysates from different sources (meat, soy bean, etc.) were examined.

A similar analysis was carried out with regard to the nitrogen source utilizable by GIN-1, the nitrogen sources tested being: ammonium ion, nitrate, amino acids or proteins.

Tables 1 and 2 summarize the carbon and nitrogen sources which are utilized by GIN-1. Table 3 summarizes more completely the chemotaxonomic analysis of the GIN-1 strain. The data presented in these Tables were obtained from a series of standard tests including diagnostic tests aimed at completely identifying and classifying the GIN-1 strain. Thus, on the basis of the results presented in these Tables it was possible to recognize the characterizing features of the GIN-1 strain when compared to closely related strains.

Analysis by standard procedures of the cell wall constituents and the fatty acid profile of the GIN-1 strain revealed the following:

The cell wall diamino acid of GIN-1 is meso-DAP. Mycolic acids are also present. The fatty acid profile shows that the major acids of GIN-1 are straight chain saturated and unsaturated acids together with branched acids having the $CH_3$ group on $C_{10}$, in particular, tuberculostearic acid (10-methyloctadecanoic acid).

TABLE 1

| Summary of the carbon and nitrogen sources utilized by GIN-1 | | | |
|---|---|---|---|
| CARBON SOURCE | GROWTH | CARBON SOURCE | GROWTH |
| Sugars: | | Proteins: | |
| Glucose | +++ | Gelatin | − |
| Mannose | ± | Casein | +++ |
| Fructose | ± | Complex media: | |
| Lactose | − | Nutrient broth | +++ |
| Maltose | ± | Luria broth | +++ |
| Xylose | − | Casitone | +++ |
| Arabinose | ± | Tryptose soy broth | +++ |
| Cellobiose | − | | |
| N-acetyl-glucosamine | ± | Yeast extract | +++ |
| Mannitol | +++ | | |
| Gluconate | ± | | |
| Organic acids: | | Amino acids: | |
| Caprate | − | Tryptophan | − |
| Adipate | ± | Alanine | +++ |

TABLE 1-continued

| Summary of the carbon and nitrogen sources utilized by GIN-1 | | | |
|---|---|---|---|
| CARBON SOURCE | GROWTH | CARBON SOURCE | GROWTH |
| Malate | +++ | Proline | +++ |
| Citrate | ± | Phenylalanine | − |
| Phenyl-acetate | − | | |

Carbon source utilization was evaluated in defined medium.
+++ = very good growth ± = poor growth − = no growth

TABLE 2

| Nitrogen sources utilized by GIN-1 for growth. | |
|---|---|
| NITROGEN SOURCE | GROWTH |
| Ammonium ion | + |
| Nitrate | − |
| Alanine | + |
| Tryptophan | − |
| Arginine | − |
| Yeast extract | + |
| Urea | ± |

Each nitrogen source was examined in a defined medium.
+ = good growth
± = poor growth
− = no growth

TABLE 3

Ability of the GIN-1 strain to decompose certain carbon and nitrogen sources and to grow on various sole carbon sources and under certain growth conditions.

| Decomposition of: | Ability to decompose: |
|---|---|
| Adenine | − |
| Tyrosine | + |
| Urea | − |

| Growth on sole carbon sources: | Growth |
|---|---|
| Inositol[1] | − |
| Maltose | − |
| Mannitol | + |
| Rhamnose | − |
| Sorbitol | + |
| m-hydroxybenzoic[2] acid | + |
| Sodium adipate | − |
| Sodium benzoate | + |
| Sodium citrate | + |
| Sodium lactate | + |
| Testosterone | − |
| L-tyrosine | + |
| Glycerol[1] | − |
| Trehalose | − |
| p-hydroxybenzoic acid[2] | (+) |
| Growth in 5% NaCl | + |
| Growth at 10° C. | (+) |
| Growth in dextrose azide[3] | − |
| ONPG | − |

[1] 1% w/v
[2] 0.1% w/v
[3] 0.02% w/v
(+) weak positive

EXAMPLE 3: The defined growth medium and growth conditions of GIN-1

A semi-defined growth medium formula, which is based on sea water has been established on the basis of the results presented in Example 2. This medium supports good growth of the bapterium. However, initially this formulation presented some difficulties concerning the rapid estimation of bacterial growth due to some salt precipitation (mainly phosphates). As a result, the final defined medium formulation was established which imitates the actual salt concentration and other conditions normally characteristic of sea water which are important for consistent cell growth, these other conditions being primarily the pH and the osmotic potential.

The aforesaid medium consists of a dissolved mixture of salts, which cover the requirements for nitrogen, phosphate, sulfur and trace elements, and supports the balanced osmotic environment for the marine bacterium. Glucose is added as the carbon source. Yeast extract is added in defined small quantities and serves as a nitrogen source and supplies a certain, yet unidentified, nutritional demand. Yeast extract has been chosen as the best supplement out of a series of other complex rich mixtures: Nutrient broth, Tryptose Soy Broth, Casitone. The concentration of yeast extract presented in Table 4a is in excess to prevent any limitation in batch cultures grown in flasks.

The concentration of one of the salts, KCl, was found to be important in supporting good growth. It was carefully optimized, meeting a concentration similar to the overall salt concentration in sea water, in particular that of the Mediterranean Sea from which the GIN-1 strain originates.

The optimal pH for growth of GIN-1 was found to be in the range between pH=6.5 to pH=7.2.

The final formula of defined medium which supported excellent growth of GIN-1 is presented in Tables 4a and 4b.

TABLE 4a

Composition of the defined growth medium for GIN-1

| CONSTITUENT | AMOUNT ADDED g/l |
|---|---|
| KCl | 40.0 |
| $(NH_4)_2SO_4$ | 4.0 |
| $MgSO_4.7H_2O$ | 0.2 |
| $K_2HPO_4.3H_2O$ | 8.9 |
| $KH_2PO_4$ | 2.9 |
| Sodium citrate | 2.0 |
| Yeast extract* | 8.0 |
| Glucose* | 6.0 |
| Trace salts solution** | 2.0 ml |

*Stock solution (concentration 20 fold) was prepared, sterilized separately, and added into the sterile medium up to the desired concentration.
**Trace salts solution according to Table 4b below.

TABLE 4b

Composition of stock solution of Trace salt solution

| CONSTITUENT | AMOUNT g/l |
|---|---|
| $FeSO_4.7H_2O$ | 0.604 |
| $CoCl_2.6H_2O$ | 0.788 |
| $MnSO_4.4H_2O$ | 0.594 |
| $CuSO_4.5H_2O$ | 0.624 |
| $ZnSO_4.7H_2O$ | 0.422 |
| $CaCl_2.2H_2O$ | 0.368 |
| $Na_2MoO_4$ | 0.696 |

The trace salt solution was prepared by dissolving the salts in water and acidifying by concentration $H_2SO_4$ to pH = 2.0. This solution was membrane filtered in cases when sterility was required.

Analysis of the temperatures at which GIN-1 is capable of growing revealed that this strain can grow at 10° C., 37° C. and 45° C.

However, the optimal temperature range for growth of GIN-1 was found to be between 28°–32° C. Temperatures below this range (down to 25° C.) supported good growth. However, temperature above the optimum resulted in a slower growth (10–20% of the optimal growth rate).

The above defined medium was used for bioadsorption studies as well as larger scale cell cultivation in a fermentor.

Transferring the GIN-1 cells (at 32° C.) from the defined medium to the sea water medium resulted in no decrease in viability and with no significant change in lag time. Similar results were obtained when transferring the cells from rich complex medium into a sea water environment or into the defined-medium.

All of the components in the aforesaid defined medium formulation are commercially available. The sugar and yeast extract sources may be replaced by concentrated mixtures of sugar and nutrients from such sources as molasses and corn steap liquor, or other readily available by-products of the food industry. These media component replacements do not lead to any adverse effect on the growth of GIN-1.

EXAMPLE 4: Small scale cell cultivation of GIN-1 i) Determination of cell mass of GIN-1

Evaluating the mass of cells by protein content determination was found to be useful when applied to bacterial cultures as well as when applied to adsorption studies with the relevant oxides in coal ash or in pure form. The protein content determination required an initial alkaline treatment of the cells by resuspending them in 0.2 N NAOH and heating the suspension for 20 minutes at 100° C. The boiled suspension was then evaluated as to its protein content by standard protein determination assays as are well known in the art, for example, the Lowry method as described.

ii) Growth rate of GIN-1

Figure 4:
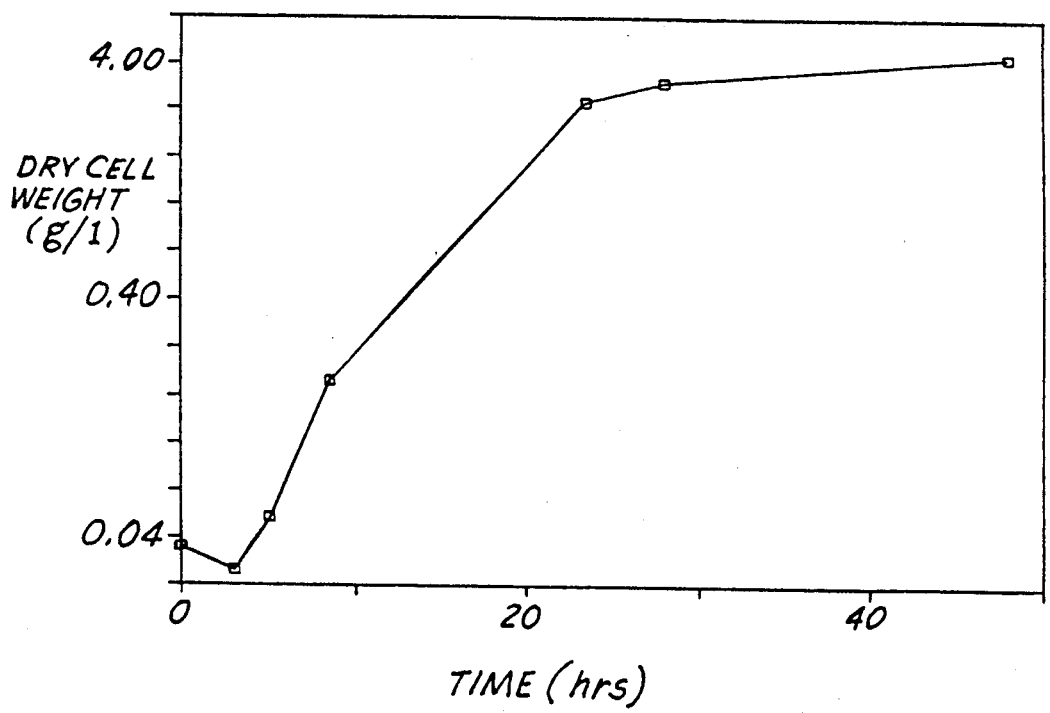
FIG. 4 is a growth curve of the GIN-1 strain of the present invention determined as described in Example 4.

The aerobic growth of the bacterium in the above medium (Example 3) at 32° C. was fast. A doubling time of 1.2 to 1.8 hours could be easily reached (specific growth rate of 0.3–0.5 $h^1$), suggesting fast and convenient cultivation on a larger scale. Routine aerobic cell cultivation in standard erlenmeyer flasks provided a cell growth of 4–6 g cells/liter (Dry Cell Weight) within 30 hours. A typical growth curve of GIN-1 is represented in FIG. 4 in which the growth conditions were as follows: The cells were cultivated in erlenmeyer flasks containing the aforementioned defined medium. The cultures were grown at 32° C. with agitation on a gyrotory shaker. Periodically, culture samples were removed and their cell mass determined in the following ways: (a) spectrophometrically by adsorbance at 660 nm in a standard spectrophometer, (b) by protein determination by the Lowry method as noted in (i) above, and (c) by dry cell weight measurements after drying washed cells at 80° C.

iii) Ratio of Protein to total cell mass of GIN-1

The observed ratio as calculated from the results obtained in (ii) above, of protein to dry cell weight of about 0.24 g/g suggests, that the bacterial cells contain large amounts of non-protein material relative to many other bacterial strains (in most unicellular bacteria this ratio is close to 0.6 g/g). The above protein to dry cell weight ratio indicates the existence of a thick polymeric envelope which surrounds the cells and might serve as protective shield for the cells and may also be involved in its adsorption capability to the oxides in coal ash. In this respect, it should be noted that gram-positive bacteria in general, contain and accumulate certain biopolymers such as teichoic acids, $\beta$-poly hydroxy butyrate and thick layers of peptidoglycans, and very often secrete these biopolymers in the form of an extracellular envelope. In this regard, as described above in Example 2, it is possible that the diamino acid, meso-DAP, of the GIN-1 strain's cell wall, the mycolic and other major fatty acids, in particular the tuberculostearic acid of this strain, which may be incorporated into an extracellular envelope, may be involved in this strain's ability to absorb the oxides in coal ash.

EXAMPLE 5: Classification and identification of GIN-1 i) Standard Diagnostic media and assays

Selective and diagnostic media have been employed for classifying and identifying the isolated strains in order to better understand their physiological characteristics. These characteristics are related to their external surface properties, in particular, their adsorption capacity for metal oxides. Further, these characteristics are important for safety reasons relating to the handling of such bacteria.

The biochemical and physiological identification of the GIN-1 strain was carried out by way of standard identification assays.

Standard kits of Biomerieux, France (api 20 ne; ATB G- #1401; ATB Staph #1402-OF) were employed in the identification purpose. Some of these kits contributed to the elucidation of certain biochemical details while others contributed to the determination of the antibiotic sensitivity profile of GIN-1.

A summary of the identifying characteristics of GIN-1 is presented in the following Tables 5 and 6.

According to the aforementioned accumulated data with regard to the identification of the GIN-1 strain it was concluded that this strain is a coryneform species, belongs to the genus Rhodococcus, and that it probably represents a new Rhodococcus species.

Upon comparison of GIN-1 with other known Rhodococcus species it was also concluded that GIN-1 does not conform well with the biochemical profiles of these species. Moreover, it was observed that the known species *Rhodococcus rhodochrous* has a biochemical profile most closely resembling that of GIN-1, differing, however, from GIN-1 in that it was capable of utilizing, as sole carbon source, maltose, sodium adipate, testosterone, glycerol and trehalose, none of which are utilizable as sole carbon sources by GIN-1 (Table 3).

As noted before, a sample of this GIN-1 strain has been deposited under No. 40340 at the National Collections of industrial and Marine Bacteria, Ltd. (NCIMB), Aberdeen, Scotland.

TABLE 5

| GIN-1 Identification properties | |
|---|---|
| • | |
| Colony, Shape and Morphology | Salmon-pink; opaque; round: regular; entire; convex; matt; and less than 0.5 mm in diameter |
| Gram | Appears in irregular packets. positive |
| Flagella | present, motility not observed |
| Utilization of carbon sources, cell wall constituents and fatty acid profile ** | (see Example 2) |
| Reduction of nitrate to nitrite | + |
| Reduction of nitrite to nitrogen | − |
| Oxidase | − |
| Catalase | + |
| Alanine dehydrogenase | + |

TABLE 5-continued

| GIN-1 Identification properties | |
|---|---|
| Phenylalanine deaminase | − |
| Proline aryl amidase | + |
| β-glucoronidase | − |
| β-D-glucosidase | − |
| β-D-xylosidase | − |
| β-D-galactosidase | − |
| Urease | − |

*Morphological data obtained from microscopic analysis as illustrated in FIGS. 3A-D. FIG. 3A shows a phase micrograph (mag. × 1000) of GIN-1 cells in culture; FIG. 3B shows a fluorescent micrograph (mag. × 1000) of the GIN-1 cells of FIG. 3A in which fluorescent label is propidium dioxide; FIGS. 3C and D show electron micrographs (mag. × 40,000) of GIN-1 cells, in which negative staining technique was used.

**Biochemical data obtained from analysis using standard kits (api 20 ne as supplied bY Biomerieux, France).

TABLE 6

| Antibiotic sensitivity of GIN-1 | | |
|---|---|---|
| Antibiotic agent | Susceptibility | conc. range mg/l |
| Penicillines gr. A. Amoxicilline | S | 4–16 |
| Amoxicilline- Ac. clavulanique | S | 4–16 |
| Oxacilline | S | 2 |
| Ureidopenicillines, meziocilline | S | 8–32 |
| Cefalosporines G, cefalotine | S | 8–32 |
| Cefalosporines G, cefotaxime | S | 4–32 |
| Cefatazidime | S | 4–32 |
| Tobramycine | S | 4–8 |
| Kanamycine, Amikacine | S | 8–16 |
| Gentamicine | S | 4–8 |
| Netilimicine | S | 4–8 |
| Cyclines, Tetracyclines | S | 4–8 |
| Quinolones G, Nalidixic acid | R | 8–16 |
| Quinolones G, pefloxacine | I | 1–4 |
| Cortimoxazole | S | 2–8 |
| Erythromycine | S | 1–4 |
| Lincomycine | S | 2–8 |
| Pristinamycine | S | 2–4 |
| Fusidic acid | S | 2–16 |
| Rifampicine | S | 4–16 |
| Vancomycine | S | 8–8 |
| Fosfomycine | R | 32–64 |

*Data is based on results obtained using ATB G- #1401 and ATB Staph #1402-OF assay kits of Biomerieux, France EXAMPLE 6: Large-scale cell cultivation of GIN-1 in a 16 liter fermenter A fed batch fermentation process was carried out in a 16 liter fermentor (SF-116, New-Brunswick), 12 liter working volume. The fermentor was con-trolled by a NBS MI-4100 multiloop controller which transmitted the data to an IBM $^R$ compatible PC AT computer. Monitoring of respiratory activity during the process was carried out using a Mass spectrometer gas analyser Hal-100 (Hiden, England) linked to the above computer for on-line calculation of the oxygen uptake rate and carbon dioxide evolution rate. The aerobic fermentation was run for 72 hours, using the defined medium formula and with supplementary feeding of dextrose (glucose) and yeast extract in response to cell mass increase and cell respiratory activity. The temperature was maintained at 32° C., aeration rate was kept at 6 liter/minute and agitation at 600 rpm. The PH in this run was independently and automatically controlled by the additions of 2 M sulfuric acid. Foam was automatically controlled by adding a 10-fold diluted solution of a Dow-Corning silicone emulsion #1520 (Belgium, supplied by Shubim, Israel).

The cell mass in the fermentation reached a concentration of over 15 g/l of cells within 30 hours. It continued to climb to over 25 g/l during the next 30 hours.

Figure 5:
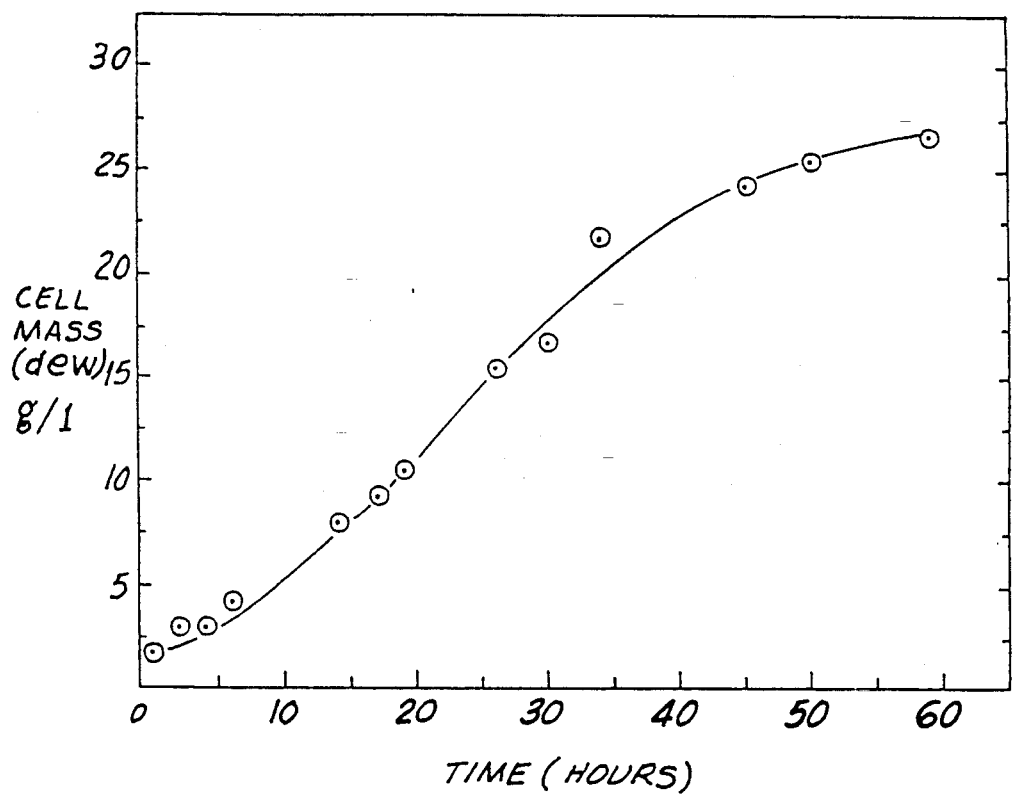
FIG. 5 is a growth curve of the GIN-1 strain of the present invention in large scale fermentation conditions as described in Example 6.

The growth pattern of GIN-1 cells in the aforesaid large-scale (16 l) controlled fermentation is shown in FIG. 5. The cell growth in FIG. 5 is expressed in terms of the measured dry cell weight (dcw) at each stage. Cell yield was about 0.36 g Cell/g sugar. Further elevations in cell concentration and in cell yield require a more intensive oxygen supply than that employed.

The above fermentation process may also use molasses as the main component of the medium.

EXAMPLE 7: Preservation of stock cultures of GIN-1 i) Long term preservation of the isolated and purified GIN-1 strain was accomplished by freezing samples of r-ell suspensions in 10% or 20% glycerol solution. Examination of viability after 12 months showed no significant decrease in cell viability (less than 2% loss of viability).

ii) Short term preservation was carried out on nutrient agar slopes or stabs. For routine culture procedures the strain was kept on nutrient-agar semi-solid medium in petri dishes.

iii) Freeze drying of GIN-1 samples is a possible alternative method of preservation.

EXAMPLE 8: Adsorption of Pure cultures of GIN-1 to metal oxides

Adsorption of the bacterium GIN-1 to $TiO_2$ was used (as noted before), as a selective parameter in the isolation of this bacterium. Once isolated and purified, our aim was to quantitate this adsorption in terms of the amount of bacterial cells adsorbed to given amounts of the oxide. The degree of adsorption was determined by measuring the non-adsorbed bacteria left in the supernatant of the oxide suspension and subtracting it from the input concentration. After incubation and periodic vigorous shaking of different amounts of cells with a constant amount of $TiO_2$ in suspension in sea water, the non-adsorbed cells were separated from the oxide and the oxide-adsorbed bacteria by low speed centrifugation (200 rpm). Protein was released from the cells by alkaline treatment and measured by the Lowry procedure (as defined hereinbefore).

Figure 6:
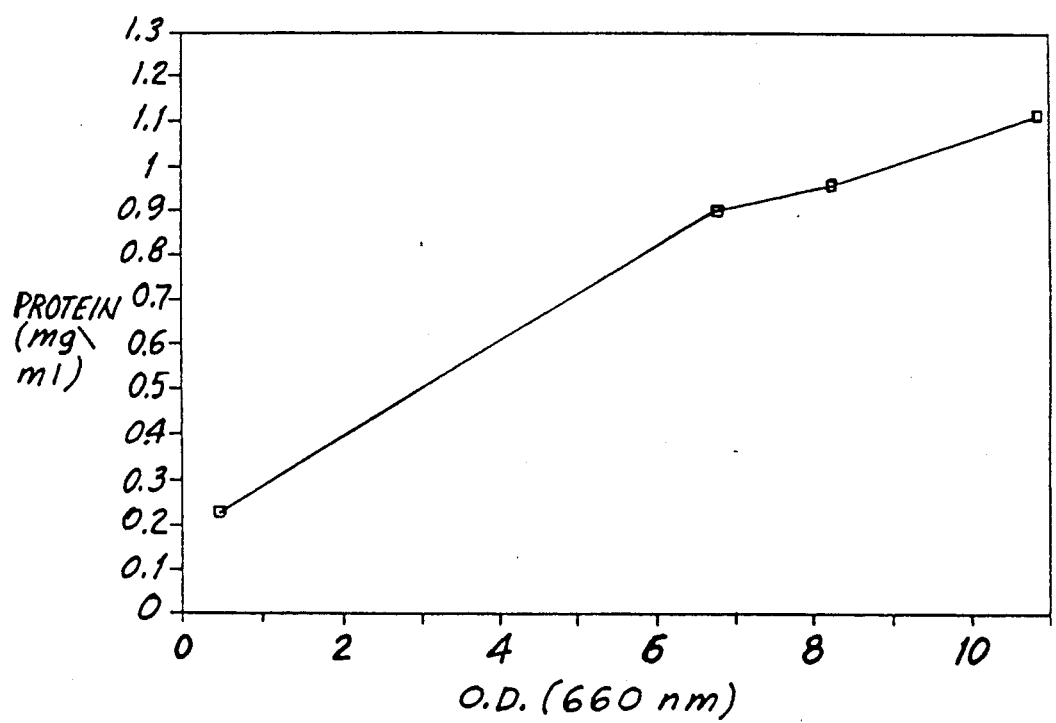
FIG. 6 is a curve illustrating the correlation between cell mass and total cell protein in a GIN-1 culture.
Figure 7:
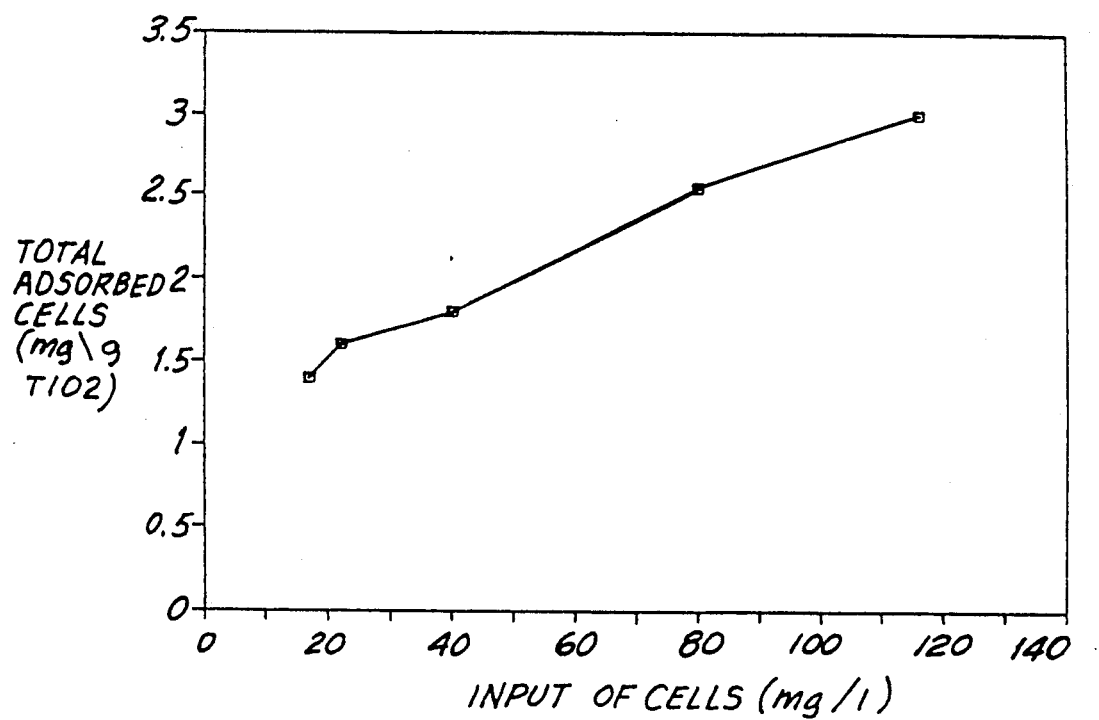
FIG. 7 is a curve illustrating the percentage of GIN-1 cells adsorbed onto T as described in Example 8.

As shown above (Examples 4 and 6), the amount of protein in the cells was found to correlate linearly with their mass as shown in FIG. 6. FIG. 7 shows the percentage of cells adsorbed onto $TiO_2$ (1% w/v) as function of the total input amounts of, cells. From these curves it is concluded that a saturation of adsorption was achieved at an input cell concentration of above 150 mg Cells/l, though the highest efficiency of adsorption was obtained at cell input of 200 mg Cells/l or 20 mg Cells per gr of $TiO_2$ (a 1:50 mass ratio of cells to $TiO_2$). Study of the amount of cells which can bind to a given mass of standard $TiO_2$ powder indicated that the saturating mass ratio of cell (as protein) to the oxide is about 1 g cell to 30 g of oxide.

The amount of cells which adsorb to an oxide under the same conditions described for $TiO_2$ was used for determining the selectivity of binding of GIN-1 to different oxides.

Figure 8:
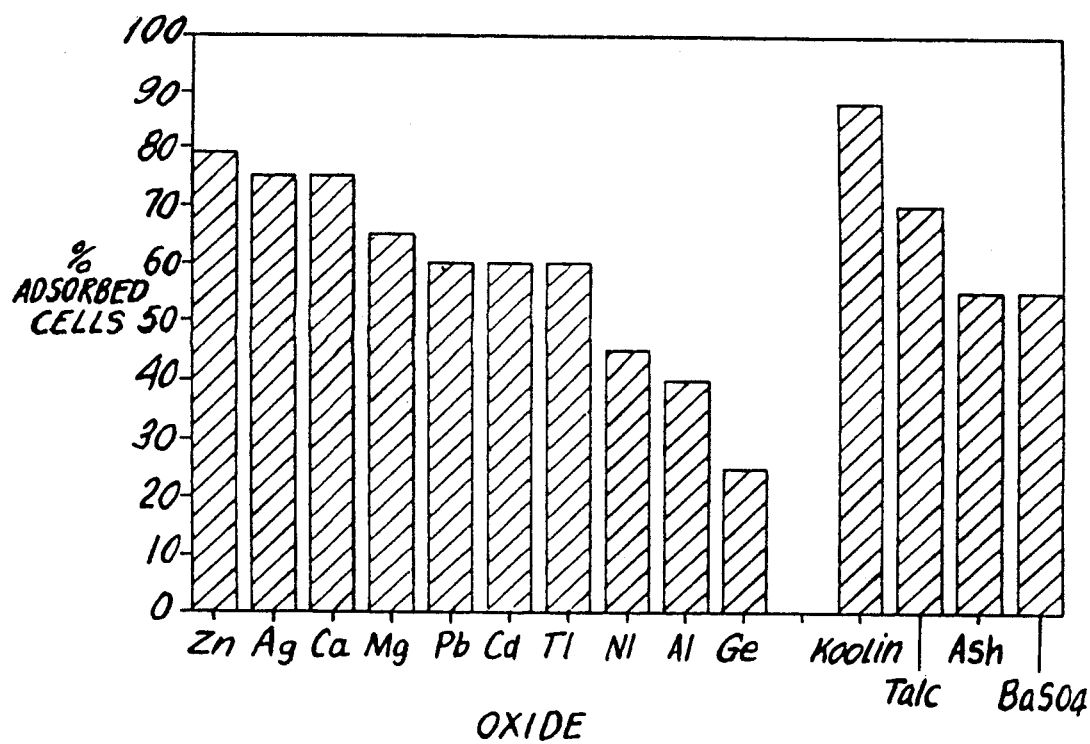
FIG. 8 is a bar graph illustrating the relative adsorption of various metal oxides to the GIN-1 strain as described in Example 9.

EXAMPLE 9: Specificity of adsorption of pure cultures of GIN-1 to various oxides including metal oxides In order to determine the specificity of metal oxide binding by the GIN-1 bacteria, bacterial cells (at the amount yielding 50% adsorption with $TiO_2$, ratio of 1:100 g/g cell to oxide, Example 8) were incubated with various metal oxides, as well as with $BaSO_4$, kaolin (hydrated aluminium silicate) and talc (magnesium silicate). The amount of adsorbed cells to each oxide was determined as described above (Example 8) for the $TiO_2$. As shown in FIG. 8, little specificity was observed under the experimental ratio of oxide to cells. All the oxides tested were adsorbed to the bacteria, highest degree of adsorption observed with kaolin (90%), lowest with $GeO_2$ (25%).

It should be emphasized that this ratio depends basically on the surface area of the oxide particles. Therefore, serious precautions should be taken when comparing the saturation level of cell adsorption to different oxides possessing different granular distribution and density. Thus, selectivity of binding to different oxides cannot be determined accurately and compared via the above method. A more reliable assay method was therefore developed as follows:

EXAMPLE 10: Establishing an assay for kinetic selectivity

As expected, binding of oxide was observed at the lower cell concentration range, as was verified with protein measurements and fluorescent labeling of the bound cells (FIGS. 9A-D). FIGS. 9A,B represent $TiO_2$ particles suspended in sea water in the absence of GIN-1 cells as visualized by fluorescent microscopy (FIG. 9A-regular phase microscopy; FIG. 9B-background fluorescence in presence of fluorescent dye, propidium iodide; in both cases magnification is ×2000).

FIGS. 9C,D represent attachment of isolated GIN-1 bacteria to $TiO_2$ particles as visualized by fluorescent labeling of cells with propidium iodide. The attachment was examined at two different ratios of cells to $TiO_2$: FIG. 9C-1:5000 cell/oxide ratio; FIG. 9D-1:500 cell/oxide ratio. It should be noted that the bacteria appear as lighted spots on the larger oxide particles. The lower concentration range of cell input is of higher practical significance from an economical point of view. For this reason, the factors affecting the obtained efficiency of adsorption (about 50%) at this low cell input were investigated and the efficiency was markedly improved by achieving better homogeneity and solid-solid mass transfer. The agitation rate of over 250 rpm of impeller mixing or gyrotory shaking with samples having a total volume of up to 500 ml and solid content of 20% w/v provided an increased adsorption efficiency to over 95%. Even under prolonged mixing of several hours, cells did not dissociate from the oxide. On the contrary, under prolonged mixing a higher degree of binding was observed-close to 99% of input cells were adsorbed.

It should be mentioned that in many previously described cases of adsorption of bacteria to various surfaces, a prolonged or intensive agitation resulted in shearing of cells from surfaces to which they had been adsorbed. The stable attachment obtained with respect to the binding of GIN-1 cells to $TiO_2$ may well stem from the surface properties of the adhering GIN-1 bacterium. Electron micrographs of the bacteria adsorbed on $TiO_2$ show that the adsorption occurs by binding of components of the cell-wall to the oxide and not by entrapment of the bacteria within the $TiO_2$ precipitate (FIG. 10A,B; where FIG. 10A shows free GIN-1 cells in culture, and FIG. 10B shows $TiO_2$ adsorbed to GIN-1 cells).

Using the above established adsorption conditions, the kinetics of the adsorption was investigated as a more reliable parameter for the determination and comparison of selectivity of adsorption by the GIN-1 cells with respect to various oxides.

EXAMPLE 11: Kinetics of adsorption of GIN-1 to oxides

Figure 11:
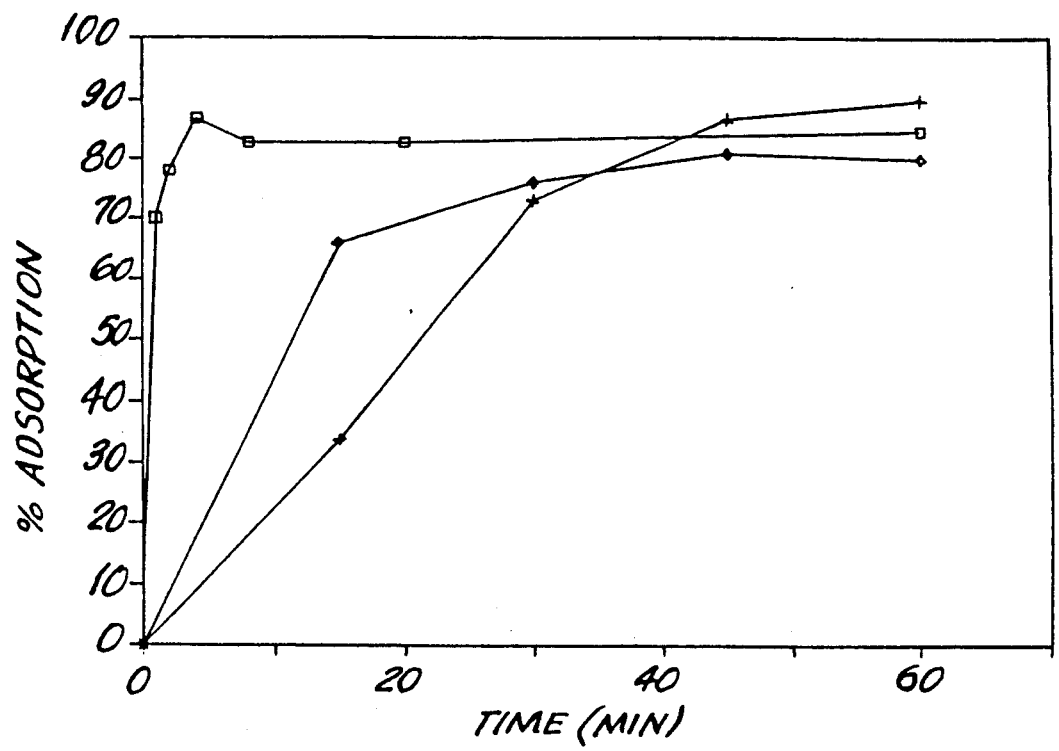
FIG. 11 is a graph of the kinetics of adsorption of GIN-1 cells to $TiO_2$, $Al_2O_3$ and $Fe_2O_3.FeO$ as described in Example 11.

The rate of adsorption of GIN-1 cells to $TiO_2$ was outstandingly fast. Using the abovementioned conditions (Example 9) the kinetics of adsorption of GIN-1 cells to $TiO_2$ was determined as was the kinetics of adsorption of GIN-1 cells to alumina ($Al_2O_3$) and magnetite ($Fe_2O_3.FeO$). The comparative kinetics of adsorption to these metal oxides are presented in FIG. 11 wherein: □ denotes $TiO_2$ adsorption kinetics; ◇ denotes $Al_2O_3$ adsorption kinetics; and +denotes $Fe_2O_3.FeO$ adsorption kinetics. Over 85% of the input cells of GIN-1 were found to adhere to the $TiO_2$ during the first 60 seconds. Over 95% of input cells were adsorbed during the next three minutes. In contrast $Al_2O_3$ and $Fe_2O_3.FeO$ adsorbed GIN-1 cells at lower rates requiring 0.5-3 hours for complete adsorption (FIG. 11).

EXAMPLE 12: GIN-1 Cell translocation from a mixture of oxides including $TiO_2$ A marked difference in the affinity of various oxides to the bacteria was observed. The interaction between GIN-1 and $TiO_2$ is very strong. Attempts to remove the adsorbed cells by treatment of the cell-oxide complex with acid, base, anionic detergent, high salt concentrations and various organic solvents failed. The strength by which the bacteria were adsorbed to the other oxides was lower than that observed with $TiO_2$. When $TiO_2$ particles suspended in sea water were mixed with alumina ($Al_2O_3$) or magnetite ($Fe_2O_3.FeO$) suspensions which were preadsorbed to GIN-1 cells, the majority of bacteria (90%) were translocated from the oxide to which they initially adsorbed and onto the unadsorbed (bare) $TiO_2$ surface. The opposite translocation of cells from $TiO_2$-cell complexes to these other oxides failed to occur. The results suggest a high attachment coefficient of the GIN-1 cells to the $TiO_2$. These translocation results are presented in Table 7.

This result was highly important for the establishment of a $TiO_2$ extraction procedure from coal ash achieved by combining the relatively rapid adsorption of cells to magnetite as a first step with the subsequent fast translocation to the $TiO_2$ to be added as a second step during which an intermediate stage of dual adsorption to both oxides occurs. Following the translocation, a complete separation of the released free magnetite and the $TiO_2$ as adhered to the bacteria may be accomplished. This procedure therefore also provides for the efficient recycling of the magnetite.

TABLE 7

Translocation of GIN-1 cells from magnetite ($Fe_2O_3.FeO$) to $TiO_2$

| a Test # | Cells adsorbed to magnetite | | Cells adsorbed to $TiO_2$ | |
|---|---|---|---|---|
| | Initial mg/g oxide | Final mg/g oxide | Initial mg/g oxide | Final mg/g oxide |
| I | 0.21 | <0.005 (<2.5)$^b$ | — | 0.19 (90)b |
| II | — | <0.002 (<0.9)$^b$ | 0.23 | 0.21 (91)$^b$ | a. Two sets of tranlocation experiments were carried out:
I. Initial adsorption of GIN-1 cells on magnetite with subsequent addition of $TiO_2$
II. Reverse procedure. Initial adsorption on $TiO_2$ and subsequent addition of magnetite.
b. The recovery of cells as % of initial cell input is given in brackets.

EXAMPLE 13: Adsorption of GIN-1 cells to coal ash

Tested by the same procedure described above (Examples 9 and 10), coal ash was found to adsorb GIN-1 approximately to the same level as $TiO_2$ and most other oxides tested. Apparently, the carbon constituent of the coal ash was not-adsorbed to the cells and formed a separate precipitated layer when the bacteria were mixed with the coal ash suspension, this in contrast to control coal ash suspension devoid of bacteria from which the carbon constituent does not separate and precipitate. These observations are illustrated in FIGS. 12A, 12B, 13A and 13B, where FIGS. 12A and 12B show electron micrographs (×850) of coal ash material in suspension without the GIN-1 bacteria, and FIGS. 13A and 13B show electron micrographs (×3000 and ×3500) of coal ash material adsorbed by the GIN-1 cells.

EXAMPLE 14: Extraction of $TiO_2$ from coal ash using the magnetic separation technique i) Extraction of $TiO_2$ enriched coal ash.

It should be noted that in this example pure $TiO_2$ powder is added to the coal ash material in order to determine the efficiency of the separation technique and whether such a technique influences the GIN-1 cells in any unforeseen way. Clearly, however, the hereindescribed magnetic separation technique is intended, for use in the extraction of metal oxides, in particular $TiO_2$, from coal ash as obtained from coal-fired power stations, and this without the addition of any pure $TiO_2$ powder.

a) A coal ash sample of 150 g gram was weighed into a 1 liter glass beaker and mixed with 4.5 g of pure $TiO_2$ powder creating a net addition of 3% of this oxide. The mixture was suspended in 750 ml of filtered sea water (1:5 solid to liquid ratio).

b). A magnetite suspension in sea water with preadsorbed GIN-1 cells having a 1:100 cell/magnetic mass ratio was added to the coal ash +$TiO_2$ Suspension to a final concentration of 0.5% w/v.

c) The mixture of (b) was initially stirred and subsequently subjected to a first magnetic separation, effectively precipitating all components which adhered to the magnetite-GIN-1 coupled sorbent. A concentrate pellet was obtained containing about 24% of the total solids input. This pellet is composed of the magnetite-GIN-1 complex to which is adhered the $TiO_2$ and the various other metal oxides from the coal ash, e.g. $Al_2O_3$ and additional $TiO_2$ (from the coal ash).

d) The above pellet was resuspended in 250 ml of sea water and the suspension was then put on top of a Heidolph magnetic stirrer without a magnetic bar. The magnetic stirrer was operated at 250 rpm causing turbulence in the suspension and exerting its attraction on the magnetic particles, concentrating them at the bottom of the beaker.

e) A moderate turbulence of the liquid due to the magnetic stirrer caused the suspended magnetic particles to rotate, shearing off a fraction of the particles from the magnetite-cell complex into the upper section of the liquid. 200 ml of the upper liquid phase containing a light grey particle mixture was decanted and a fresh 250 ml volume of sea water was added. Again, the suspension was allowed to reach the moderate turbulence state driven by the magnetic field and a second portion of the originally attached particles was released into the upper liquid phase. Four such sequential separation steps were carried out.

f) The four upper phase fractions were combined and the slightly grey solid material was collected in the form of a pellet by centrifugation (6000 rpm 10 min.).

g) After drying this pellet it was weighed, yielding 9.3 g of white material.

h) A sample of this material was dissolved in 10 sulfuric acid at 80° C. and analysed for its composition by Atomic adsorption. The results showed that the material contained: about 57% $TiO_2$, about 35% $Al_2O_3$ and the rest of the material comprised mainly calcium, magnesium and ferrous oxides.

ii) Extraction of $TiO_2$ from coal ash by the magnetic separation technique

A similar experiment as detailed in (i) above was conducted using only coal ash as the source for extractable oxides. All steps were carried out identically. A total of 5.3 g of white material was collected at the end of the extraction procedure (step (g) above). The final dried white material contained about 11% $TiO_2$, 42% $Al_2O_3$ and the rest of the material contained mainly the additional calcium, magnesium and ferrous oxides.

It should be noted, however, that it is possible to achieve selective extraction of the individual metal oxides from the coal ash by exploiting the kinetic adsorbance properties of the GIN-1 strain which, (as detailed in Examples 10 and 11) show a preference for $TiO_2$ adsorption especially in the first few minutes when $TiO_2$ is added to the cells. Thus, the adsorption period of the magnetite-cell complex with the coal ash may be limited to a short period, that is, up to 1 minute at which time the adsorbed complex is magnetically sedimented followed by the subsequent separation of the adsorbed particles. This should provide a final extract comprising mainly $TiO_2$.

Conversely, the coal ash may be incubated with the bacteria for a long period in which case substantially all the metal oxides will be removed from the coal ash and recovered as a mixture of oxides. The non-adsorbed material which represents some 40% of the starting coal ash material may also be collected. This non-adsorbed material consists of unburned carbon and silicates (sand), from which the carbon may be separated and recycled as fuel for the power plant, while the sand, devoid of the toxic metal oxides may be safely discarded in landfills. The extracted metal oxide mixture may then be separated by the aforementioned procedures by exploiting the kinetic of adsorption properties of the GIN-1 strain.

Figure 14:
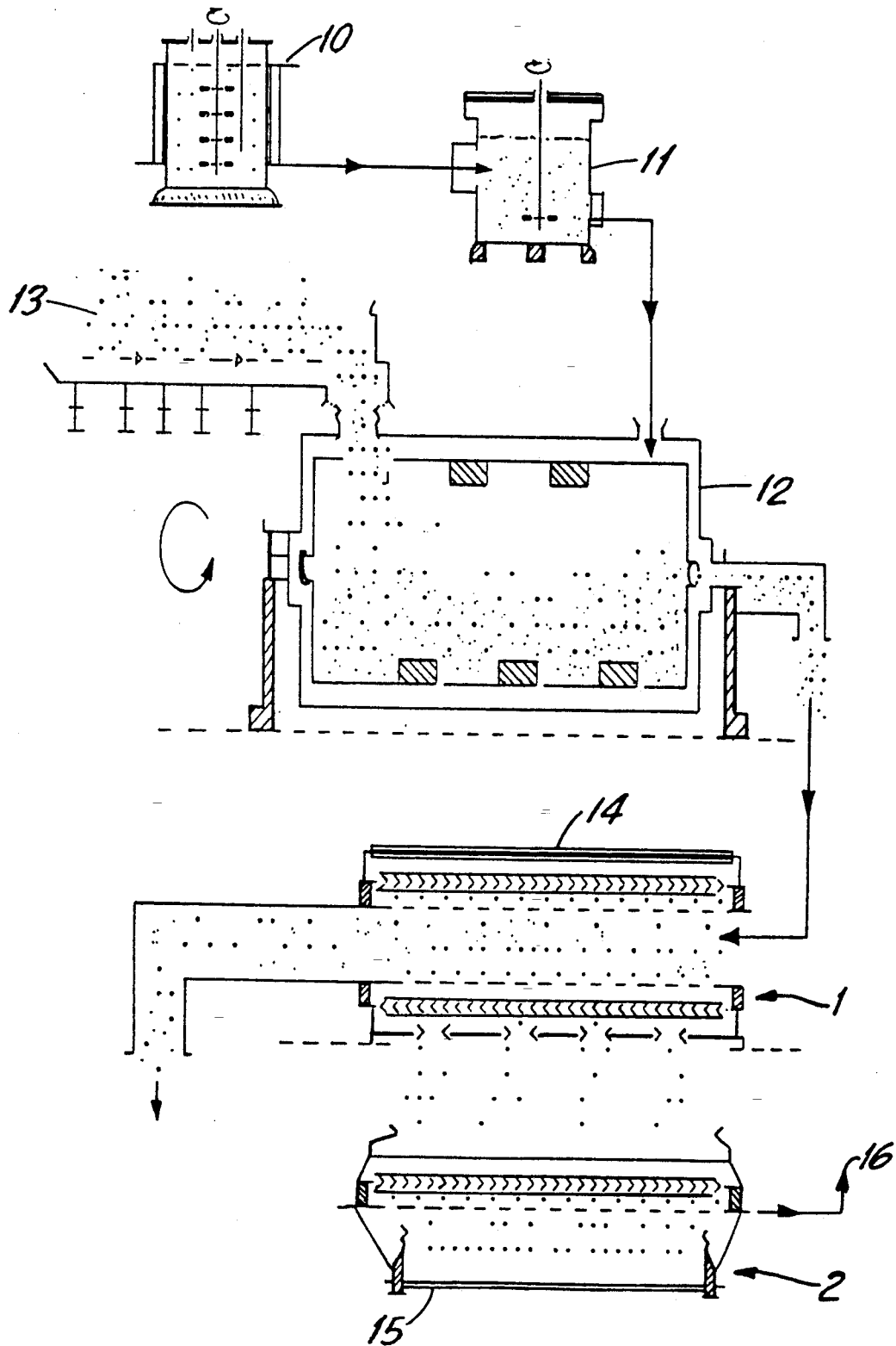
FIG. 14 is a schematic representation of a modified process according to the invention with magnetic separation as described in Example 15.

EXAMPLE 15: Establishment of the magnetically assisted separation-extraction process for extracting $TiO_2$ from coal ash The procedure involves the following steps, as schematically illustrated in FIG. 14:

a) Initial adsorption in adsorption reactor 11, of GIN-1 bacteria grown in fermentor 10, to magnetite, to form a magnetic biosorbent;

b) Addition and mixing of the magnetic biosorbent from adsorption reactor 11, with coal ash supplied via conveyor 13;

c) continuous magnetic separation of the metal oxides from the coal ash mixture in second reactor 12, sequentially connected to magnetic separators 14 and 15, to be kinetically regulated as noted above (Examples 11 and 12) to lead to preferential $TiO_2$ adsorption;

d) Desorption and separation of the magnetite 16, in separator 15, from the $TiO_2$-GIN-1 complex, based on the above-noted replacement (Example 12) of magnetite on GIN-1 cells by the $TiO_2$ particles;

e) Removal of GIN-1 cells from $TiO_2$, by collecting the GIN-1-$TiO_2$ and then complex from separator 15, drying it burning it to remove the cells, leaving mainly the $TiO_2$.

We claim:

1. A pure culture of a Gram-positive bacterial strain designated GIN-1 being a member of the genus Rhodococcus and deposited under No. 40340 at the National Collections of Industrial and Marine Bacteria Ltd. (NCIMB) at Aberdeen, Scotland, said strain having an ability to grow in an aqueous saline solution and to adsorb to metal oxides in an aqueous environment.

* * * * *